United States Patent [19]

Stemp et al.

[11] Patent Number: 5,232,938

[45] Date of Patent: Aug. 3, 1993

[54] CERTAIN 1,2,4-TRIAZOLE(OXY OR AMINO)BENZOPYRAN DERIVATIVES HAVING PHARMACOLOGICAL ACTIVITY

[75] Inventors: Geoffrey Stemp; Gordon Burrell, both of Cumbria, England

[73] Assignee: Beecham Grop p.l.c., England

[21] Appl. No.: 873,587

[22] Filed: Apr. 21, 1992

Related U.S. Application Data

[63] Continuation of Ser. No. 527,020, May 22, 1990, abandoned.

[30] Foreign Application Priority Data

May 24, 1989 [GB] United Kingdom ............... 8911949

[51] Int. Cl.⁵ .................. C07D 249/12; C07D 249/14; C07D 405/12; A61K 31/41
[52] U.S. Cl. ..................................... 514/383; 514/384; 548/263.2; 548/263.8; 546/114; 546/115
[58] Field of Search ........................... 548/263.2, 263.8; 514/383, 384

[56] References Cited

FOREIGN PATENT DOCUMENTS 205292 12/1986 European Pat. Off. ............ 546/115
2204868 11/1988 United Kingdom ................ 549/265

*Primary Examiner*—Alan L. Rotman
*Attorney, Agent, or Firm*—Rosenman & Colin

[57] ABSTRACT

Compounds of formula (I) and pharmaceutically acceptable salts thereof:

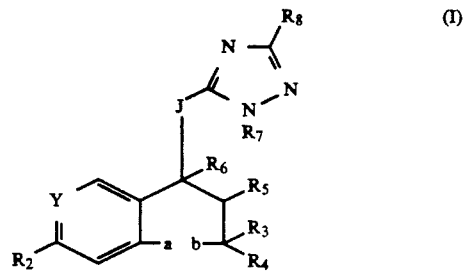

wherein a, b, J, Y and $R_2$–$R_8$ are as defined herein are potassium channel activators, a process for their preparation and their pharmaceutical use.

12 Claims, No Drawings

CERTAIN 1,2,4-TRIAZOLE(OXY OR AMINO)BENZOPYRAN DERIVATIVES HAVING PHARMACOLOGICAL ACTIVITY

CROSS-REFERENCE

This application is a continuation of Ser. No. 07/527,020 filed May 22, 1990 now abandoned.

This invention relates to novel compounds having pharmacological activity, to a process for their preparation and to their use as pharmaceuticals.

EP-A-76075, 91748, 107423, 139992, 168619, 205292, 214818, 250077 and 321175 (Beecham Group p.l.c.) describe benzopyran, tetrahydronaphthalene, pyranopyridine and indane derivatives having antihypertensive and/or bronchodilator activity.

EP-A-277611 and 277612 (Hoechst Aktiengesellschaft), EP-A-314446 (American Home Products Corporation) WO 89/07103 (Nissan Chemical Industries Limited) and EP-A-363883 (Merck Patent Gesellschaft mit Beschränkter Haftung), describe further classes of benzopyran derivatives.

A novel group of compounds has been discovered, which compounds have a triazoleamino substituent at the 4-position of the benzopyran, (or equivalent other position when other than a benzopyran). These compounds are believed to be potassium channel activators, useful in the treatment of disorders associated with smooth muscle contraction, such as cardiovascular disorders including hypertension, congestive heart failure, angina, peripheral vascular disease, cerebral vascular disease and pulmonary hypertension. Other disorders include those of the gastrointestinal tract, respiratory system, uterus and urinary tract. Such disorders include irritable bowel syndrome and diverticular disease; reversible airways obstruction including asthma; premature labour; incontinence and kidney stones. They may also be of potential use in the treatment of epilepsy.

Accordingly, the present invention provides a compound of formula (I) or a pharmaceutically acceptable salt thereof:

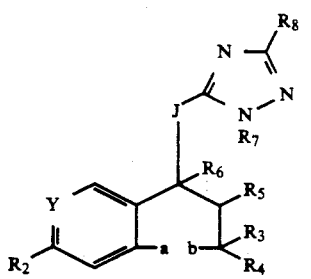

wherein
a and b together form an —O— linkage or a bond or (when $R_2$ is hydrogen), $CH_2$;
J is O or NH;
either Y is N and $R_2$ is hydrogen; or
Y is C-$R_1$ wherein
either one of $R_1$ and $R_2$ is hydrogen and the other is nitro, cyano, halo, $CF_3$, $C_2F_5$, formyl, aldoxime, $CF_3O$, $NO_2$—CH=CH—, NC—CH=CH—; a group $R_xX$— wherein $R_x$ is $C_{1-6}$ alkyl, aryl or heteroaryl either of which may be optionally substituted by one, two or three of $C_{1-4}$ alkyl, $C_{1-4}$ alkoxy, nitro, halo, $CF_3$ and cyano; and X is C=O, O.C=O, C=O.O, CHOH, SO, $SO_2$, O.SO, $O.SO_2$, CONH, O.CONH, C=S, O.C=S, C=S.O, CH.SH, SONH, $SO_2NH$, O.SONH, $O.SO_2NH$, CO—CH=CH, C=NHOH, C=$NNH_2$; or a group $R_yR_zNZ$— wherein $R_y$ and $R_z$ are independently hydrogen or $C_{1-6}$ alkyl and Z is C=O, SO or $SO_2$; or a group $(R_wO)_2P(O)W$ wherein $R_w$ is hydrogen or $C_{1-6}$ alkyl and W is O or a bond; or $R_1$ is a $C_{3-8}$ cycloalkyl group or a $C_{1-6}$ alkyl group optionally substituted by a group which is hydroxy, $C_{1-6}$ alkoxy, amino optionally substituted by one or two $C_{1-6}$ alkyl groups, $C_{1-7}$ alkanoylamino, $C_{3-8}$ cycloalkyloxy or $C_{3-8}$ cycloalkylamino; and $R_2$ is hydrogen; or one of $R_1$ and $R_2$ is nitro, cyano or $C_{1-3}$ alkylcarbonyl and the other is a different group selected from nitro, cyano, halo, $C_{1-3}$ alkylcarbonyl, methoxy or amino optionally substituted by one or two $C_{1-6}$ alkyl or by $C_{2-7}$ alkanoyl; or $R_1$ and $R_2$ together with the carbon atoms to which they are attached, form 2,1,3-oxadiazole;
either one of $R_3$ and $R_4$ is hydrogen or $C_{1-4}$ alkyl and the other is $C_{1-4}$ alkyl; or
$R_3$ and $R_4$ together are $C_{2-5}$ polymethylene;
$R_5$ is hydrogen, hydroxy, $C_{1-6}$ alkoxy or $C_{1-7}$ acyloxy; and
$R_6$ is hydrogen; or
$R_5$ and $R_6$ together form a bond;
$R_7$ is $C_{1-6}$ alkyl or phenyl $C_{1-4}$ alkyl optionally substituted in the phenyl ring by up to three moieties selected from $C_{1-4}$ alkyl, $C_{1-4}$ alkoxy or halo; and
$R_8$ is amino, hydrogen or methyl.

There is a group of compounds within formula (I) wherein
J is NH;
either Y is N and $R_2$ is hydrogen; or
Y is C—$R_1$ wherein
either one of $R_1$ and $R_2$ is hydrogen and the other is nitro, cyano, halo, $CF_3$, formyl, aldoxime, $NO_2$—CH=CH—, NC—CH=CH—; a group $R_xX$— wherein $R_x$ is $C_{1-6}$ alkyl, aryl or heteroaryl either of which may be optionally substituted by one, two or three of $C_{1-4}$ alkyl, $C_{1-4}$ alkoxy, nitro, halo, $CF_3$ and cyano; and X is C=O, O.C=O, C=O.O, CHOH, SO, $SO_2$, O.SO, $O.SO_2$, CONH, O.CONH, C=S, O.C=S, C=S.O, CH.SH, SONH, $SO_2NH$, O.SONH, $O.SO_2NH$, CO—CH=CH, C=NHOH, C=$NNH_2$; or a group $R_yR_zNZ$— wherein $R_y$ and $R_z$ are independently hydrogen or $C_{1-6}$ alkyl and Z is C=O, SO or $SO_2$; or $R_1$ is a $C_{3-8}$ cycloalkyl group or a $C_{1-6}$ alkyl group optionally substituted by a group $R_9$ which is hydroxy, $C_{1-6}$ alkoxy, amino optionally substituted by one or two $C_{1-6}$ alkyl groups, $C_{1-7}$ alkanoylamino, $C_{3-8}$ cycloalkyloxy or $C_{3-8}$ cycloalkylamino and $R_2$ is hydrogen; or one of $R_1$ and $R_2$ is nitro, cyano or $C_{1-3}$ alkylcarbonyl and the other is a different group selected from nitro, cyano, halo, $C_{1-3}$ alkylcarbonyl, methoxy or amino optionally substituted by one or two $C_{1-6}$ alkyl or by $C_{2-7}$ alkanoyl;

either one of $R_3$ and $R_4$ is hydrogen or $C_{1-4}$ alkyl and the other is $C_{1-4}$ alkyl; or
$R_3$ and $R_4$ together are $C_{2-5}$ polymethylene;
$R_5$ is hydrogen, hydroxy, $C_{1-6}$ alkoxy or $C_{1-7}$ acyloxy;
$R_6$ is hydrogen;
$R_7$ is methyl and $R_8$ is amino; and
the triazoleamino moiety is trans to the $R_5$ group when $R_5$ is hydroxy, $C_{1-6}$ alkoxy or $C_{1-7}$ acyloxy.

a and b together preferably form an —O— linkage.

J is preferably NH.

Y is preferably C—$R_1$.

When either one of $R_1$ and $R_2$ is hydrogen, the other is preferably selected from halo, $CF_3$, $C_{1-6}$ alkylcarbonyl, $C_{1-6}$ alkoxycarbonyl, nitro or cyano.

When one of $R_1$ and $R_2$ is nitro, cyano or $C_{1-3}$ alkylcarbonyl the other is, favourably, amino optionally substituted by one or two $C_{1-6}$ alkyl groups or by $C_{2-7}$ alkanoyl. In particular, when one of $R_1$ and $R_2$ is nitro, cyano or acetyl, the other is amino, methylamino, dimethylamino or acetylamino. Preferably, when one of $R_1$ and $R_2$ is nitro or cyano, especially cyano, the other is amino.

Halo substituents in $R_1$ and/or $R_2$ or $R_7$ are usually chloro or bromo.

Values for $R_x$ when alkyl in $R_1/R_2$ are usually selected from methyl, ethyl, n- and iso-propyl, n-, iso-, sec- and tert-butyl preferably methyl or ethyl. Suitable examples of other alkyl or alkyl containing groups in $R_1$ and in $R_3$, $R_4$ and $R_7$ when alkyl include those listed for $R_1$ and $R_2$ alkyl groups.

A sub-group of $R_x$ heteroaryl is 5- or 6-membered monocyclic or 9- or 10-membered bicyclic heteroaryl of which 5- or 6-membered monocyclic heteroaryl is preferred. In addition, 5- or 6-membered monocyclic or 9- or 10-membered bicyclic heteroaryl preferably contains one, two or three heteroatoms which are selected from the class of oxygen, nitrogen and sulphur and which, in the case of there being more than one heteroatom, are the same or different. Examples of 5- or 6-membered monocyclic heteroaryl containing one, two or three heteroatoms which are selected from the class of oxygen, nitrogen and sulphur include furyl, thienyl, pyrryl, oxazolyl, thiazolyl, imidazolyl and thiadiazolyl, and pyridyl, pyridazyl, pyrimidyl, pyrazyl and triazyl. Preferred examples of such groups include furanyl, thienyl, pyrryl and pyridyl, in particular 2- and 3-furyl, 2- and 3-pyrryl, 2- and 3-thienyl, and 2-, 3- and 4-pyridyl. Examples of 9- or 10-membered bicyclic heteroaryl containing one, two or three heteroatoms which are selected from the class of oxygen, nitrogen and sulphur include benzofuranyl, benzothienyl, indolyl and indazolyl, quinolyl and isoquinolyl, and quinazonyl. Preferred examples of such groups include 2- and 3-benzofuranyl, 2- and 3-benzothienyl, and 2- and 3-indolyl, and 2- and 3-quinolyl.

Preferred examples of the groups or atoms for optional substitution of $R_x$ when aryl or heteroaryl include methyl, methoxy, hydroxy, chloro, nitro or cyano.

$R_1$ is preferably nitro, cyano, acetyl, $CF_3$, $C_2F_5$, methyl, ethyl, isopropyl or cyclopentyl.

Preferably $R_3$ and $R_4$ are both methyl groups.

Suitable examples of $R_5$ when alkoxy include methoxy, ethoxy, n- and iso-propoxy, of which methoxy is preferred. When $R_5$ is $C_{1-7}$ acyloxy it is usually $C_{1-7}$ carboxylic acyloxy, such as $C_{1-7}$ alkanoyloxy wherein the alkyl moiety is usually as listed for alkyl in $R_1$ and $R_2$ above.

$R_5$ is favourably hydroxy or hydrogen, preferably hydroxy.

$R_7$ is preferably methyl.

$R_8$ is preferably amino.

Examples of pharmaceutically acceptable salts include acid addition salts with acids such as hydrochloric, hydrobromic, phosphoric, sulphuric, citric, tartaric, lactic or acetic acid.

The compounds of formula (I) have at least one asymmetric centre and therefore exist in more than stereoisomeric form. The invention extends to each of these forms individually and to mixtures thereof, such as racemates.

The triazoleamino moiety may be cis or trans to the $R_5$ group when $R_5$ hydroxy, $C_{1-6}$ alkoxy or $C_{1-7}$ acyloxy. The trans configuration is preferred.

The compounds of formula (I) and their salts may form solvates, such as hydrates, and there are included as part of the invention, wherever a compound of formula (I) or a salt thereof is herein referred to.

A preferred group of compounds within formula (I) is of formula (II):

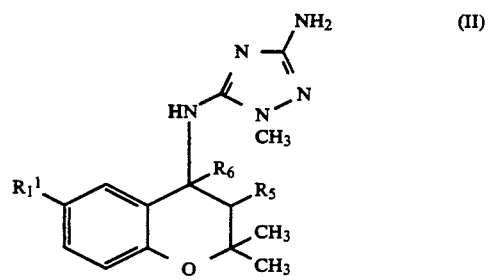

(II)

wherein $R_1^1$ is nitro, cyano, acetyl, $CF_3$, methyl, ethyl, isopropyl or cyclopentyl; and $R_5$ and $R_6$ are as defined in formula (I).

Suitable and preferred values for the variables are as described for the corresponding variables in formula (I).

The invention therefore provides a process for the preparation of a compound of formula (I), or a pharmaceutically acceptable salt thereof, which process comprises the reaction of a compound of formula (III):

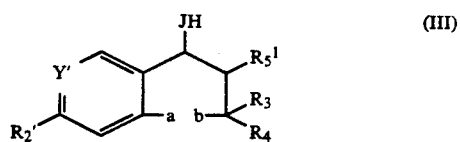

(III)

with a compound of formula (IV):

(IV)

wherein $R_5^1$ is hydrogen or hydroxy, L is a leaving group, and either E is a leaving group and $R_9$ is CN or $R_9$ and E are moieties which are capable of joining to form a triazole; and the remaining variables are as hereinbefore defined; and thereafter, when E is a leaving group, reacting the resulting compound with $R_7NNH_2$, optionally converting $R_8$ amino to $R_8$ is hydrogen, $R_5^1$ to $R_5$, Y' and/or $R_2'$ to Y and/or $R_2$ as desired or necessary; and thereafter optionally forming a pharmaceutically acceptable salt thereof.

Suitable examples of $R_9$ and E which are capable of joining to form a triazole and appropriate synthetic methods are as described in GB 2075007A and 2023133A (Glaxo Group Limited), and the descriptions and examples hereinafter. A particular example is a compound of the structure (V):

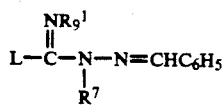

(V)

wherein $R_9^1$ is cyano or acetyl and the remaining variables are as hereinbefore defined. The compound of formula (v) wherein $R_9^1$ is cyano will form an $R_8$ is amino compound of formula (I) and the $R_9^1$ is acetyl compound will form the corresponding $R_8$ is methyl compound.

Suitable and preferred values for L include those described hereinafter for E when a leaving group.

The reaction when E is a leaving group, preferably takes place in an inert solvent, such as alcohols (e.g. ethanol), dimethylformamide or acetonitrile, preferably at elevated temperatures.

Suitable values for E then include $C_{1-6}$ alkylthio, chloro, $C_{1-6}$ alkoxy or phenoxy, preferably methylthio.

The reaction takes place in a suitable solvent, such as acetonitrile, at 0° C. to reflux at preferably ambient temperature, followed by heating under reflux for a period of approximately 24 hours. The process is as described by B. T. Heitke and C. J. McCarty J. Org. Chem., 39, 1974, p.1522.

$R_8$ when amino may be converted to $R_8$ is hydrogen by conventional deamination methods, by converting to the diazonium salt using nitrous acid and subsequent treatment with hypophosphorus acid.

$R_5^1$ is hydroxy may be converted to alkoxy or acyloxy by conventional alkylation/acylation methods; and to $R_5$ and $R_6$ is a bond by dehydration, as described in the aforementioned patent publications.

Conversions of $Y'$ to $Y$ and $R_2'$ to $R_2$ are conventional in the art of aromatic chemistry.

Pharmaceutically acceptable salts may be formed conventionally.

Intermediates of the formula (III) wherein J is NH are known and may be prepared according to the methods described in the aforementioned Patent Publications. Intermediates of the formula (III) wherein J is O may be prepared from the corresponding 3,4 epoxy compounds, also described in the aforementioned patent publications, by hydrolysis with acid (cis and trans) or base (trans only).

It will be appreciated that the method employing the compound of formula (IV) wherein E is a leaving group will produce a mixture of products on formation of the triazole ring and the required product of formula (I) separated out by conventional methods, such as crystallisation or chromatographic techniques. The method employing compounds of the formula (v) is usually preferred.

The compounds of formula (I) have been found to have blood-pressure lowering activity, useful in the treatment of hypertension, and/or bronchodilator activity. They are also believed to be of potential use in the treatment of other disorders hereinbefore referred to.

The present invention accordingly provides a pharmaceutical composition which comprises a compound of formula (I) or a pharmaceutically acceptable salt thereof, and a pharmaceutically acceptable carrier. In particular, the present invention provides an anti-hypertensive or bronchodilator pharmaceutical composition which comprises an effective amount of a compound of formula (I) or a pharmaceutically acceptable salt thereof, and a pharmaceutically acceptable carrier.

The compositions are preferably adapted for oral administration. However, they may be adapted for other modes of administration, for example parenteral administration for patients suffering from heart failure. Other alternative modes of administration include sublingual or transdermal administration. A composition may be in the form of spray, aerosol or other conventional method of inhalation, for treating respiratory tract disorders.

The compositions may be in the form of tablets, capsules, powders, granules, lozenges, suppositories, reconstitutable powders, or liquid preparations, such as oral or sterile parenteral solutions or suspensions.

In order to obtain consistency of administration it is preferred that a composition of the invention is in the form of a unit dose.

Unit dose presentation forms for oral administration may be tablets and capsules and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulphate.

The solid oral compositions may be prepared by conventional methods of blending, filling or tabletting. Repeated blending operations may be used to distribute the active agent throughout those compositions employing large quantities of fillers. Such operations are of course conventional in the art. The tablets may be coated according to methods well known in normal pharmaceutical practice, in particular with an enteric coating.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilized before filling into a suitable vial or ampoule and sealing. Advantageously, adjuvants such as a local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10-60% by weight, of the active material, depending on the method of administration.

The compounds of formula (I) and pharmaceutically acceptable salts thereof are believed to show a synergistic effect with ACE inhibitor or β-blocker antihypertensive agents and such combination products, for concomitant or sequential administration, form an aspect of the present invention.

The present invention further provides a method of prophylaxis or treatment of hypertension in mammals including man, which comprises administering to the suffering mammal an anti-hypertensive effective amount of a compound of formula (I) or a pharmaceutically acceptable salt thereof.

An effective amount will depend on the relative efficacy of the compound, the severity of the disorder being treated and the weight of the sufferer. However, a unit dose form of a composition of the invention may contain from 0.05 to 500 mg of a compound of the invention and more usually from 0.1 to 50 mg, for example 0.5 to 25 mg such as 0.5, 1, 2, 5, 10, 15 or 20 mg. Such compositions may be administered from 1 to 6 times a day, more usually from 1 to 4 times a day, in a manner such that the daily dose is from 0.01 to 25 mg for a per kg body weight and more particularly from 0.1 to 10 mg/kg.

No toxicological effects are indicated at the aforementioned dosage ranges.

The present invention further provides a compound of formula (I) or a pharmaceutically acceptable salt thereof for use in the treatment or prophylaxis of hypertension and/or respiratory tract disorders.

The tables show the intermediates and compounds of the invention prepared.

The following descriptions relate to the preparation of intermediates and the following examples relate to the preparation of compounds of formula (I).

TABLE 1

(intermediates)

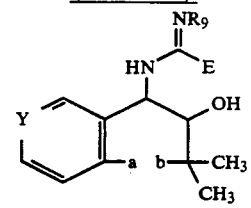

| No. | Y | a, b | $R_9$ | E |
|-----|-----|------|-------|------|
| D2 | NC—C | —O— | CN | $SCH_3$ |
| D3 | N | —O— | CN | $SCH_3$ |
| D4 | $C_2H_5$—C | —O— | CN | $SCH_3$ |
| D5* | NC—C | —O— | CN | N—N=CHPh<br>\|<br>$CH_3$ |
| D7 | NC—C | a bond | CN | $SCH_3$ |

TABLE 1-continued (intermediates)

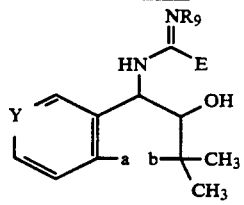

| No. | Y | a, b | $R_9$ | E |
|-----|-----|------|-------|------|
| D8 | Ac-C | —O— | CN | $SCH_3$ |

NB. $R_5^1$ and $HN(C=NR_9)E$ moieties are trans
*(3S,4R)-isomer

TABLE 2

(Compounds of formula (I))

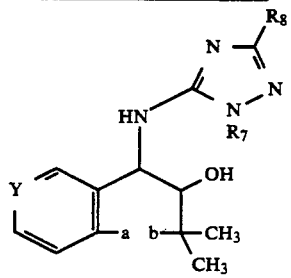

| No. | Y | a, b | $R_7$ | $R_8$ |
|-----|-----|------|-------|-------|
| E1 | NC—C | —O— | $CH_3$ | $NH_2$ |
| E2 | NC—C | —O— | $CH_3$ | H |
| E3 | NC—C | —O— | $CH_2Ph$ | $NH_2$ |
| E4 | NC—C | —O— | $CH_3$ | $CH_3$ |
| E5 | N | —O— | $CH_3$ | $NH_2$ |
| E6 | $C_2H_5$—C | —O— | $CH_3$ | $NH_2$ |
| E7* | NC—C | —O— | $CH_3$ | $NH_2$ |
| E8 | NC—C | a bond | $CH_3$ | $NH_2$ |
| E9 | Ac—C | —O— | $CH_3$ | $NH_2$ |

*(3S,4R)-isomer

Description 1 (Preparation of starting materials for D5)

(±)-trans-4-Amino-6-cyano-3,4-dihydro-2,2-dimethyl-2H-1-benzopyran-3-ol

Sodium hydride (80% dispersion in oil, 13.7 g) was added in portions over 1h to a stirred solution of (±)-trans-3-bromo-6-cyano-3,4-dihydro-2,2-dimethyl-2H-benzopyran-4-ol (124.3 g) in tetrahydrofuran (250 ml) kept under a dry nitrogen atmosphere. The mixture was stirred for an additional 0.5 h after which a solution of the 3,4-epoxide resulted. Ethanol (620 ml) followed by 0.880 ammonium hydroxide (375 ml) were added, and the resulting mixture stirred at 60°-65° C. for 12 h before cooling to room temperature. The organic solvents were evaporated off and the aqueous residue acidified with 5N hydrochloric acid (125 ml). The mixture was then washed well with dichloromethane (total used=1.0 L) before basifying with 40% aq. sodium hydroxide (80 ml). It was then re-extracted with dichloromethane (4×250 ml) and the combined extracts washed once with brine and then dried ($Na_2SO_4$). Evaporation afforded the product as a gum which crystallised. This was broken up and triturated with a mixture of isopropyl ether and dichloromethane before filtering off and washing with further isopropyl ether. The product was dried under suction and finally under vacuum.

Yield: 83.5 g (87%) m.p.116°-117° C.

δ(CDCl$_3$): 1.21 (s, 3H); 1.51 (s, 3H); 2.10 (b, 3H); 3.30 (d, J=10 Hz, 1H); 3.65 (d, J=10 Hz, 1H), 6.82 (d, J=8 Hz, 1H); 7.42 (m, 1H) 7.74 (m, 1H)

Resolution of (±)-trans-4-Amino-6-cyano-3,4-dihydro-2,2-dimethyl-2H-1-benzopyran-3-ol The title compound (100 g) was dissolved in propan-2-ol (500 ml) with stirring and heating to 70° C. Water (250 ml) was added followed by (+)-ammonium 3-bromo-camphor-9-sulphonate (150.5 g). The mixture was stirred and warmed back to 70° C. to effect dissolution. 5N Hydrochloric acid (80 ml) was then added fairly rapidly until the mixture reached pH5. It was then cooled to 55° C. before seeding with authentic crystalline product. The mixture was cooled to room temperature before filtering off the product and washing with a mixture of isopropyl alcohol (50 ml) and water (25 ml). After drying in air at 50° C. the yield of 3-bromo-camphor-9-sulphonic acid salt of the (+)-isomer of the title compound was 75 g (31%).

[α]$_D^{20}$ (C=1, MeOH)= +88.9°, m.p. 288°-291° C.

δ(d$_6$-DMSO): 0.81 (s, 3H); 1.07 (s, 3H); 1.15 (s, 3H); 1.10-1.25 (m, 1H); 1.45 (s, 3H); 1.66-1.88 (m, 2H); 2.05-2.20 (m, 1H), 2.36 (d, J=14 Hz, 1H); 2.83 (d, J=14 Hz, 1H); 2.97 (ss, J=6,6 Hz, 1H); 3.64 (dd, J=6,10 Hz, 1H); 4.30 (d, J=10 Hz, 1H); 5.00 (d, J=6 Hz, 1H); 6.42 (d, J=6 Hz, 1H); 7.04 (d, J=8 Hz, 1H); 7.76 (m, 1H); 8.07 (bs, 1H); 8.53 (bs, 3H).

The foregoing salt (75 g) was dissolved in a solution of potassium hydroxide (10.3 g) in water (50 ml) and the mixture extracted with dichloromethane (4×250 ml). The combined extracts were washed once with brine and dried (Na$_2$SO$_4$). Evaporation afforded the (+)-isomer of the title compound as a glassy solid (30.5 g; 99%). Crystallisation from ethyl acetate-petrol afforded prisms of m.p. 85°-86° C.

[α]$_D^{20}$ (C=1, MeOH)+82.4°.

Methyl-N-acetyl-1-methyl-2-(phenylmethylene)hydrazinecarboximidothioate

Methyl-1-methyl-2-(phenylmethylene)hydrazinecarboximidothioate-hydroiodide* (4 g) and triethylamine (2.5 g) were dissolved in dichloromethane (50 ml). To this solution acetyl chloride (1.05 g) was added slowly maintaining temperature below 20° C. The mixture was stirred at room temperature in a dry nitrogen atmosphere for 1.5 h. The organic residues were washed with water (5×20 ml), dried over anhydrous sodium sulphate and the solvent removed in vacuo giving a yellow solid which upon trituration with ether gave the title compound (2.30 g) as an off-white solid of m.pt. 102°-104° C.

$^1$H NMR (CDCl$_3$) δ: 2.28 (s,3H), 2.86 (s,3H) 3.43 (s,3H), 7.40 (m,3H), 7.70 (m,3H).

Description 2

N'-Cyano-N-4-(trans-6-cyano-3,4-dihydro-2,2-dimethyl-2H-benzopyran-3-ol)carbamimidothioic acid methyl ester (D2)

A solution of trans-4-amino-6-cyano-3,4-dihydro-2,2-dimethyl-2H-benzopyran-3-ol (3.5 g) and dimethyl N-cyanodithioiminocarbonate (2.42 g) in acetonitrile (5 ml) was heated in an oil bath at 90° C. under a stream of dry nitrogen for 48 h. Evaporation of the solvent gave a yellow glass which was chromatographed on silica gel (Kieselgel 60; with gradient elution; 100% chloroform-2% methanol 98% chloroform) giving the title compound as a white solid (4.8 g) of m.p. 216°-218° C. (Dec.).

$^1$H-nmr (d$_6$-DMSO) δ1.16 (s, 3H); 1.41 (s, 3H); 2.63 (s, 3H); 3.79 (dd, J=6, 10 Hz, 1H); 5.07 (dd, J=9, 10 Hz, 1H); 5.94 (d, J=6 Hz, 1H); 6.96 (d, J=9 Hz, 1H); 7.52 (d, J=2 Hz, 1H); 7.64 (dd, J=2, 9 Hz, 1H); 8.57 (d, J=9 Hz, 1H).

Description 3

N'-cyano-N-4-]3,4-dihydro-2,2-dimethyl-2H-pyrano-(3,2 c)pyridin-3-ol]carbamimidothioic acid methyl ester (D3)

A solution of trans-4-amino-3,4-dihydro-2,2-dimethyl-2H-pyrano(3,2,c)pyridin-3-ol (1.94 g) and dimethyl-N-cyanodithioiminocarbonate (1.46 g) in acetonitrile was heated at 70°-80° C. under nitrogen for 48 h. The crystals formed after cooling were filtered off giving the title compound (2.1 g) as a colourless solid of m.pt. 180°-182° C. $^1$H NMR (DMSOd$_6$) δ: 1.15 (s,3H), 1.42 (s,3H), 2.64 (s,3H), 3.80 (dd,J=6,10 Hz,1H), 5.10 (dd,J=9,10 Hz,1H), 5.98 (d,J=6 Hz,1H), 6.80 (d,J=6 Hz,1H), 8.17 (s,1H), 8.26 (m,1H), 8.63 (d,J=9 Hz,1H).

Description 4

N'-Cyano-N-4-(trans-6-ethyl-3,4-dihydro-2,2-dimethyl-2H-1-benzopyran-3-ol)-carbamimidothioic acid methyl ester (D4)

A solution of trans-4-amino-6-ethyl-3,4-dihydro-2,2-dimethyl-2H-1-benzopyran-3-ol (2.0 g) and dimethyl-N-cyano-dithioiminocarbonate (1.32 g) in acetonitrile (10 ml) was heated at 70°-80° C., under nitrogen for 48 h. Evaporation of solvent in vacuo, and chromatography of the residue on silica gel, eluting with 3% methanol-chloroform gave the title compound (2.8 g) m.pt. 167°-169° C.

$^1$H nmr (DMSOd$_6$) δ: 1.10 (t,3H), 1.12 (s, 3H), 1.37 (s,3H), 2.5 (q,2H), 2.62 (s,3H), 3.74 (dd,J=6,10 Hz,1H), 5.06 (dd,J=9,10 Hz,1H), 5.75 (d,J=6 Hz,1H), 6.70 (d,J=9 Hz,1H), 6.84 (d,J=2 Hz,1H), 7.00 (dd,J=9,2 Hz,1H), 8.60 (d,J=10 Hz,1H).

Description 5

(3S,4R)-N'-Cyano-N''-[1-methyl-2-(phenylmethylene)-hydrazine]-N-4-(6-cyano-3,4-dihydro-2,2-dimethyl-2H-1-benzopyran-3-ol)quanidine (D5)

A solution of (3S,4R)-6-cyano-3,4-dihydro-2,2-dimethyl-4-amino-2H-1-benzopyran-3-ol (3.62 g) and N-cyano-1-methyl-2-(phenylmethylene)hydrazine-carboximidothioic acid, methyl ester (5.12 g) in dry pyridine (6 ml) was heated at 90° C., for 6 days, under nitrogen. The solution was evaporated in vacuo, and the residue triturated with toluene. The solid was filtered, and recrystallised from acetone-ethyl acetate to give the title compound (1.98 g) as a colourless solid having m.pt. 259°-61° C. [α]$^{20}$D (c=1.002, DMSO)= +23.55°.

Anal. Found: C,65.67; H,5.56; N,20.91%. C$_{22}$H$_{22}$N$_6$O$_2$ requires: C,65.66; H,5.51; N,20.88%.

Description 6 (preparation of starting materials for D7)

a) trans-5-Cyano-1,1-dimethyl-3-azido-indan-2-ol

A mixture of 5-cyano-1,1-dimethyl-2,3-epoxyindane (1.34 g), sodium azide (0.533 g), and ammonium chloride (0.44 g) in dry N,N-dimethylformamide (20 ml) was stirred and heated at 60° C., under nitrogen, for 3 h. The mixture was diluted with water, and extracted with ethyl acetate. The combined organic layers were washed with water, brine, and then dried ($Na_2SO_4$). Removal of solvents in vacuo, followed by chromatography of the residue (Si gel, eluted with 30% EtOAc in pentane) gave the title compound as a gum (0.93 g).
I.R. 2125, 2140 cm$^{-1}$.

Mass Spectrum: Found: M+228.1011; $C_{12}H_{12}N_4O$ requires M+228.1011.

b) trans-5-Cyano-1,1-dimethyl-3-amino-indan-2-ol

A solution of trans-5-cyano-1,1-dimethyl-3-azido-indan-2-ol (0.93 g), triethylamine (1.2 ml) and 1,3-propanedithiol (0.9 ml) in dry methanol (20 ml) was stirred at room temperature for 48 h. After filtration, the solution was evaporated in vacuo to give the title compound (0.79 g) as a gum.

$^1H$ nmr (DMSO-d6) δ1.05 (s, 3H), 1.34 (s, 3H), 2.7–3.4 (br s, 3H), 3.57 (d, J=8 Hz, 1H), 4.05 (d, J=8 Hz, 1H), 7.28 (d, J=8 Hz, 1H), 7.65 (s, 1H).

Description 7

N'-Cyano-N-3-(trans-5-cyano-1,1-dimethylindan-2-ol)carbamimidothioic acid methyl ester (D7)

A solution of trans-5-cyano-1,1-dimethyl-3-aminoindan-2-ol (0.79 g) and dimethyl-N-cyanodithioiminocarbonate (0.57 g) in acetonitrile (10 ml) was heated at 70°–80° C. for 24 h. The solvent was removed in vacuo, and the residue chromatographed (Si gel, eluted with 10% methanol:chloroform) to give the title compound as an off-white solid (1.05 g) having m.pt. 120°–122° C.

$^1H$ nmr (DMSO-hd6) δ1.02 (s, 3H), 1.30 (s, 3H), 2.65 (s, 3H), 4.07 (dd, J=6, 10 Hz, 1H), 5.30 (d, J=10 Hz, 1H), 5.70 (d, J=6 Hz, 1H), 7.48 (d, J=9 Hz, 1H), 7.62 (d, J=2 Hz, 1H), 7.77 (dd, J=9, 2 Hz, 1H), 8.30 (s, 1H)

Description 8

N'-Cyano-N-4-(trans-6-acetyl-3,4-dihydro-2,2-dimethyl-2H-benzopyran-3-ol)carbamimidothioic acid methyl ester (D8)

The title compound was prepared from trans-4-amino-6-acetyl-3,4-dihydro-2,2-dimethyl-2H-benzopyran-3-ol (EP-A-126311), according to the method of Description 2.

EXAMPLE 1

N$^5$-[trans-4-(6-Cyano-2,3-dihydro-2,2-dimethyl-2H-benzopyran-3-ol)]-1-methyl-1H-1,2,4-triazole-3,5-diamine (E1)

Methylhydrazine (0.26 ml) was added to a solution of N$^1$-cyano-N-4-(trans-6-cyano-3,4-dihydro-2,2-dimethyl-2H-benzopyran-3-ol)carbaminidothioic acid methyl ester (D1) (1.5 g) in acetonitrile (10 ml), and the solution maintained at room temperature for 20 h, then heated under reflux for a further 24 h. A further portion of methylhydrazine (0.26 ml) was added and the mixture heated under reflux for 4 days. On cooling the solid was filtered, and washed with acetonitrile to give the title compound as a white crystalline solid (0.77 g). Recrystallisation from acetonitrile gave a sample of m.pt. 260°–261° C.

$^1$H-nmr (d$_6$-DMSO) δ1.15 (s, 3H); 1.41 (s, 3H); 3.33 (s, 3H); 3.67 (d.d., J=5, 11 Hz, 1H); 4.60 (d.d., J=8, 11 Hz, 1H); 4.92 (s, 2H); 5.84 (d, J=5 Hz, 1H); 6.66 (d, J=8 Hz, 1H); 6.92 (d, J=9 Hz, 1H); 7.60 (m, 2H).

EXAMPLE 2 trans-N$^5$-4-[6-Cyano-3,4-dihydro-2,2-dimethyl-2H-benzopyran-3-ol]amino-1-methyl-1H-1,2,4-triazole (E2)

N$^5$-trans-4-(6-Cyano-3,4-dihydro-2,2-dimethyl-2H-benzopyran-3-ol)-1-methyl-1H-1,2,4-triazole-3,5-diamine (600 mg) was dissolved in 14M sulphuric acid (2.3 ml) and the mixture cooled to −5° C. Sodium nitrite (64 mg) in water (0.5 ml) was added maintaining temperature below −3° C. Stirring and cooling were continued for 30 min.

Hypophosphorus acid (4.3 ml) was added and the mixture left to stand at 4° C. for 72 h. The aqueous phase was extracted via ethyl acetate (3×15 ml). The organic phase was washed with water (2×10 ml) sodium carbonate solution (2×10 ml) and brine (1×10 ml), dried over anhydrous sodium sulphate and solvent removed in vacuo giving a glass which was column chromatographed on silica gel eluting with ethyl acetate to give the title compound (100 mg) as a cream solid of m.pt. 247°–249° C.

Analysis: Found: C,59.99; H,5.71; N,23.17%. $C_{15}H_{17}N_5O_2$. Required: C,60.19; H,5.72; N,23.4%.

EXAMPLE 3 trans-N$^5$-4-[6-Cyano-3,4-dihydro-2,2-dimethyl-2H-benzopyran-3-ol]-1-benzyl-1H-1,2,4-triazole-3,5-diamine (E3)

A solution of N'-cyano-N-4-[trans-6-cyano-3,4-dihydro2,2-dimethyl-2H-1-benzopyran-3-ol]carbamimidothioic acid- methyl ester (D1) (0.5 g), benzyl-hydrazinedihydrochloride (0.344 g) and triethylamine (0.5 ml) in acetonitrile (4 ml) was heated under reflux in a stream of dry nitrogen for 17 h after which further benzyl-hydrazine-di-hydrochloride (0.344 g) and triethylamine (0.5 ml) were added. Heating under reflux, under N$_2$ was continued for 15 h. The solid produced was filtered, taken up in ethyl acetate (40 ml) and the organics washed with water (3×20 ml), dried over anhydrous sodium sulphate and the solvent removed in vacuo giving a foamy yellow solid which was column chromatographed on silica gel eluting with 100% ethyl acetate then 100% methanol to give a white solid (0.320 g) which was chromatographed using HPLC (Spherisorb.55, ODSl, eluted with 45% methanol, 55% 0.05M aqueous ammonium acetate, pH 5) to give the title compound (28 mg).

$^1$H NMR (CDCl$_3$): δ1.22 (s,3H), 1.47 (s,3H), 3.42–4.04 (brs,3H) overlapping 3.62(d,J=8 Hz,1H), 3.78 (d,J=8 Hz,1H), 4.63 (t,J=8 Hz,1H), 5.00 (dd,J=38,12 Hz,2H), 6.84 (d,J=8 Hz,1H), 6.95 (d,J=2 Hz,1H), 7.27 (m,2H), 7.44 (m,4H).

EXAMPLE 4 trans-N$^5$-4-[6-Cyano-3,4-dihydro-2,2-dimethyl-2H-benzopyran-3-ol]amino-1,3-dimethyl-1H-1,2,4-triazole (E4)

A solution of methyl-N-acetyl-1-methyl-2-(phenyl-methylene)hydrazine-carboximidothioate (D2) (500 mg) and trans-4-amino-6-cyano-3,4-dihydro-2,2-dimethyl-2H-benzopyran-3-ol (437 mg) in pyridine (5 ml) was heated to 50° C. in a stream of dry nitrogen for 72 h. Evaporation of the solvent gave a gum which was taken up in acetone (10 ml) and 5M hydrochloric acid (2.2 ml). Mixture was heated under reflux for 36 h. Water (30 ml) was added and aqueous extracted via ethyl acetate (4×10 ml). Combined organics were washed with sodium hydrogen carbonate solution (2×20 ml) and water (1×20 ml), dried over anhydrous sodium sulphate and the solvent removed in vacuo. Column chromatography on silica gel, gradient elution 100% chloroform to 50% chloroform, 50% methanol followed by recrystallisation from ethyl acetate/ether gave title compound as a beige solid of m.pt. 277°–280° C.

$^1$H NMR (DMSOd$_6$): δ1.34 (s,3H), 1.52 (s,3H), 2.42 (s,3H), 3.21–4.19 (brs,1H) overlapping 3.72 (s,3H), 3.80 (d,J=8 Hz,1H), 5.07 (t,J=8 Hz,8 Hz,1H), 7.06 (d,J=8 Hz,1H), 7.77 (dd,J=8,2 Hz,1H), 8.07 (d,J=2 Hz,1H), 8.88 (d,J=8 Hz,1H).

EXAMPLE 5

N$^5$-[trans-4-(3,4-Dihydro-2,2-dimethyl-2H-[3,2,c]pyranopyridine)]-1-methyl-1H-1,2,4-triazole-3,5-diamine (E5)

A solution of N'-cyano-N-4[3,4-dihydro-2,2-dimethyl-2H-pyrano-(3,2,c)pyridine-3-ol]-carbaminidothioic acid, methyl ester (D3) (0.5 g) and methylhydrazine (0.082 g) in ethanol (30 ml) was heated under reflux, under a stream of dry nitrogen for 6 h. Evaporation of the solvent gave a yellow solid (0.880 g) which was column chromatographed on silica gel with gradient elution 10% methanol 90% chloroform to 30% methanol 70% chloroform, giving a white solid (800 g). This was then flash column chromatographed eluting with 7.5% methanol 92.5% chloroform to give the title compound as a white solid (0.100 g) of m.pt. 243°–244° C.

$^1$H NMR (DMSOd$_6$) δ: 1.17 (s,3H), 1.41 (s,3H), 3.31 (s,3H), 3.66 (dd,J=9,5 Hz,1H), 4.66 (dd, J=9,8 Hz,1H), 4.89 (s,2H), 5.83 (d,J=5 Hz,1H), 6.62 (d,J=8 Hz,1H), 6.75 (d,J=6 Hz,1H), 8.20 (d,J=6 Hz,1H), 8.32 (s,1H).

EXAMPLE 6

N$^5$-[trans-4-(6-Ethyl-3,4-dihydro-2,2-dimethyl-2H-1-benzopyran-3-ol)]-1-methyl-1H-1,2,4-triazole-3,5-diamine (E6)

A solution of N'-cyano-N-4-(trans-6-ethyl-3,4-dihydro-2,2-dimethyl-2H-1-benzopyran-3-ol)-carbamimidothioic acid methyl ester (D4) (0.5 g) and methylhydrazine (150 mg, 0.17 ml) in ethanol (15 ml) was heated under reflux, under nitrogen, for 5 h. The solvent was evaporated and the residue chromatographed (silica gel, eluting with 8% methanol-ethyl acetate). Recrystallisation from ethyl acetate gave the title compound as a colourless solid having m.pt. 204°–206° C.

$^1$H NMR (DMSOd$_6$) δ: 1.08 (t,3H), 1.10(s, 3H), 1.36 (s,3H), 2.48 (q,2H), 3.30 (s,3H), 3.58 (dd,J=9,5 Hz,1H), 4.61 (dd,J=9,8 Hz,1H), 4.90 (s,2H), 5.65 (d,J=5 Hz,1H), 6.52 (d,J=8 Hz,1H), 6.65 (d,J=8 Hz,1H), 6.97 (dd,J=8, Hz,1H), 7.05 (d,J=2 Hz,1H).

EXAMPLE 7

(3S,4R)-N$^5$-[trans-4-(6-Cyano-3,4-dihydro-2,2-dimethyl-2H-1-benzopyran-3-ol)]-1-methyl-1H-1,2,4-triazole-3,5-diamine (E7)

(3S,4R)-N'-Cyano-N'''-[1-methyl-2-(phenylmethylene)hydrazine]-N-4-(6-cyano-3,4-dihydro-2,2-dimethyl-2H-1-benzopyran-3-ol)guanidine (D5) (1.98 g) was dissolved in acetone (60 ml) and treated with 5N HCl (10 ml). The mixture was stirred at room temperature for 1.5 h, then solvent was evaporated in vacuo. The residue was extracted with ether/pentane (1:1) and the aqueous layer basified with potassium hydroxide. The precipitate was filtered, dried in vacuo, and recrystallised from acetonitrile to give the title compound (1.01 g) [α]$^{20}$D (c=1.04 in MeOH)=−63.65°.

EXAMPLE 8

N$^5$-(trans-5-Cyano-1,1-dimethylindan-2-ol)-1H-2N-methyl-1,2,4-triazol-3,5-diamine (E8)

A solution of N$^1$-cyano-N-3-(trans-5-cyano-1,1-dimethylindan-2-ol)carbamimidothioic acid methyl ester (0.5 g) and methylhydrazine (0.77 g) in ethanol (30 ml) was heated under reflux, under N$_2$ for 6 hours. The solvent was removed in vacuo and the residue column chromatographed, eluting with 10% methanol/90% chloroform. HPLC on Spherisorb ODS1, eluting with 16% acetonitrile/84% 0.05M ammonium acetate gave the title compound as a white solid (16 mg).

$^1$H NMR (DMSO d$_6$) 1.02 (s,3H), 1.31 (s,3H), 3.36 (s,3H), 3.88 (d,J=6 Hz,1H), 4.86 (dd,J=8.2 Hz,1H), overlapping 4.91 (s,2H), 5.88 (brs,1H), 6.65 (d, J=6 Hz,1H), 7.45 (d,J=8 Hz,1H), 7.52 (s,1H), 7.72 (d,J=8 Hz,1H).

EXAMPLE 9

N$^5$-[trans-4-(6-Acetyl-2,3-dihydro-2,2-dimethyl-2H-benzopyran-3-ol)]-1-methyl-1H-1,2,4-triazole-3,5-diamine (E9)

The title compound was prepared from D8 in a similar manner to the compound of Example 1. m.pt. 285°–290° (decomp.).

PHARMACOLOGICAL DATA

Antihypertensive Activity

Systolic blood pressures were recorded by a modification of the tail cuff method described by I. M. Claxton, M. G. Palfreyman, R. H. Poyser, R. L. Whiting, European Journal of Pharmacology, 37, 179 (1976). A W+W BP recorder, model 8005 was used to display pulses. Prior to all measurements rats were placed in a heated environment (33.5°±0.5° C.) before transfer to a restraining cage. Each determination of blood pressure was the mean of at least 6 readings. Spontaneously hypertensive rats (ages 12–18 weeks) with systolic blood pressures >180 mmHg were considered hypertensive.

The results were as follows:

| Compound | Dose (mg/kg) | % b.p. fall* |
|---|---|---|
| E1 | 0.1 | 30 |
| E2 | 0.3 | 22 |
| E4 | 1.0 | 22 |
| E7 | 0.05 | 45 |

*maximum at 1–4 hours post dose.

2. Bronchodilator Activity

Male guinea pigs (300–600 g) were stunned by a blow to the head and bled from the carotid artery. The trachea was exposed, dissected free of connective tissue, and transferred to oxygenated Krebs solution at 37° C. Next, spirals (2 per trachea) were prepared by cutting the whole trachea spirally along its longitudinal axis and then dividing this spiral lengthwise. Each preparation was mounted, using silk thread, in a 10 ml organ bath filled with Krebs solution at 37° C. and bubbled with 5% CO$_2$ with O$_2$. The resting tension of the preparations was set at 2 g and changes in muscle tension were monitored isometrically by means of a UFI (2 oz) force and displacement transducer (Ormed Ltd) connected to a Linseis pen recorder. All preparations were allowed to equilibrate for 60 minutes. Duringthis equilibration period the preparations were washed by upward displacement at 15 minute intervals and, if necessary, the resting tension was readjusted to 2 g using a mechanical micromanipulator system.

Once a steady resting tension had been obtained, the preparations were dosed simultaneously with the test compound ($10^{-8}$–$2 \times 10^{-5}$M), and finally a maximum relaxation achieved by addition of $10^3$M isoprenaline. The fall in tension evoked by the test compound was expressed as a percentage of the total relaxation evoked in the presence of $10^{-3}$ isoprenaline. Appropriate concentration-relaxation curves were then constructed and values for potency ($IC_{50}$) were obtained.

The composition of Krebs solution is: sodium chloride 118.07 mM, sodium hydrogen carbonate 26.19 mM, potassium chloride 4.68 mM, potassium orthophosphate 1.18 mM, magnesium sulphate septahydrate 1.8 mM and calcium chloride 2.52 mM;pH ca. 7.45.]

The compound E1 gave an $IC_{50}$ value of 4 μmol.

We claim:

1. A compound of formula (I) or a pharmaceutically acceptable salt thereof:

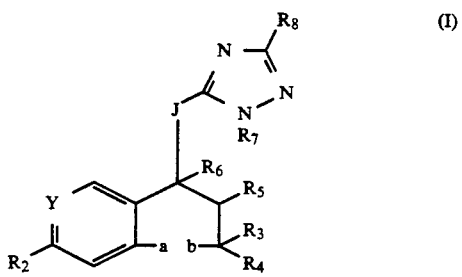

wherein
- a and b together form an —O— linkage and complete a 6- membered ring;
- J is O or NH;
- Y is C—$R_1$ wherein
  either one of $R_1$ and $R_2$ is hydrogen and the other is nitro, cyano, halo, $CF_3$, $C_2F_5$, formyl, aldoxime, $CF_3O$, $NO_2$—CH=CH—, NC—CH=CH—; a group $R_xX$— wherein $R_x$ is $C_{1-6}$ alkyl, or phenyl optionally substituted by a member selected from the group consisting of $C_{1-4}$ alkyl, $C_{1-4}$ alkoxy, nitro, halo, $CF_3$ and cyano; and X is C=O, O.C=O, C=O.O, CHOH, SO, $SO_2$, O.SO, $O.SO_2$, CONH, O.CONH, $O.SO_2NH$, CO—CH=CH, C=NHOH, C=$NNH_2$; or a group $R_yR_zNZ$— wherein $R_y$ and $R_z$ are independently hydrogen or $C_{1-6}$ alkyl and Z is C=O, SO or $SO_2$; or a group $(R_wO)_2P(O)W$ wherein $R_w$ is hydrogen or $C_{1-6}$ alkyl and W is O or a bond; or
  $R_1$ is a $C_{3-8}$ cycloalkyl group or a $C_{1-6}$ alkyl group optionally substituted by a group which is hydroxy, $C_{1-6}$ alkoxy, amino optionally substituted by one or two $C_{1-6}$ alkyl groups, $C_{1-7}$ alkanoylamino, $C_{3-8}$ cycloalkyloxy or $C_{3-8}$ cycloalkylamino; and $R_2$ is hydrogen; or
  one of $R_1$ and $R_2$ is nitro, cyano or $C_{1-3}$ alkylcarbonyl and the other is a different group selected from nitro, cyano, halo, $C_{1-3}$ alkylcarbonyl, methoxy or amino optionally substituted by one or two $C_{1-6}$ alkyl or by $C_{2-7}$ alkanoyl; or
  either one of $R_3$ and $R_4$ is hydrogen or $C_{1-4}$ alkyl and the other is $C_{1-4}$ alkyl; or
- $R_3$ and $R_4$ together are $C_{2-5}$ polymethylene;
- $R_5$ is hydrogen, hydroxy, $C_{1-6}$ alkoxy or $C_{1-7}$ acyloxy; and
- $R_6$ is hydrogen; or
- $R_5$ and $R_6$ together form a bond;
- $R_7$ is $C_{1-6}$ alkyl or phenyl $C_{1-4}$ alkyl optionally substituted in the phenyl ring by up to three moieties selected from $C_{1-4}$ alkyl, $C_{1-4}$ alkoxy or halo; and
- $R_8$ is amino, hydrogen or methyl.

2. A compound according to claim 1 wherein $R_1$ is nitro, cyano, acetyl, $CF_3$, $C_2F_5$ or $C_{1-4}$ alkyl, and $R_2$ is hydrogen.

3. A compound according to claim 1 wherein $R_1$ is cyano.

4. A compound according to claim 1 wherein $R_3$ and $R_4$ are both methyl groups.

5. A compound according to claim 1 wherein $R_5$ is hydroxy and $R_6$ is hydrogen and the triazoleamino moiety is trans to $R_6$.

6. A compound according to claim 1 wherein $R_7$ is methyl.

7. A compound according to claim 1 wherein $R_8$ is amino.

8. A method of treatment of respiratory tract disorders in mammals which comprises the administration to the mammal in need of such treatment, an effective amount of a compound according to claim 1.

9. A method of treatment of hypertension in mammals which comprises the administration to the mammal in need of such treatment, an effective amount of a compound according to claim 1.

10. A method of treatment of urinary tract disorders in mammals which comprises the administration to the mammal in need of such treatment, an effective amount of a compound according to claim 1.

11. A composition useful in the treatment of hypertension, respiratory tract disorders and urinary tract disorders in mammals, which comprises an effective amount of a compound according to claim 1 and an inert diluent or carrier therefor.

12. A compound selected from the group consisting of:
$N^5$-[trans-4-(6-cyano-2,3-dihydro-2,2-dimethyl-2H-benzopyran-3-ol)]-1-methyl-1H-1,2,4-triazole-3,5-diamine,
trans-$N^5$-4-[(6-cyano-3,4-dihydro-2,2-dimethyl-2H-benzopyran-3-ol]amino-1-methyl-1H-1,2,4-triazole,
trans-$N^5$-4-[6-cyano-3,4-dihydro-2,2-dimethyl-2H-benzopyran-3-ol]-1-benzyl-1H-1,2,4-triazole-3,5-diamine,
trans-$N^5$-4-[6-cyano-3,4-dihydro-2,2-dimethyl-2H-benzopyran-3-ol]amino-1,3-dimenthyl-1H-1,2,4-triazole,
$N^5$-[trans-4-ethyl-3,4-dihydro-2,2-dimethyl-2H-benzopyran-3-ol)]-1-methyl-1H-1,2,4-triazole-3,5-diamine,
(3S,4R)-$N^5$-[trans-4-(6-cyano-3,4-dihydro-2,2-dimethyl-2H-1-benzopyran-3-ol)]-1-methyl-1H-1,2,4-triazole-3,5-diamine, and
$N^5$-[trans-4-(6-acetyl-2,3-dihydro-2,2-dimethyl-2H-benzopyran-3-ol)]-1-methyl-1H-1,2,4-triazole-3,5-diamine.

* * * * *